United States Patent
Ladas

(10) Patent No.: US 12,201,513 B2
(45) Date of Patent: Jan. 21, 2025

(54) SYSTEMS, APPARATUSES, AND METHODS FOR INTRAOCULAR LENS SELECTION USING ARTIFICIAL INTELLIGENCE

(71) Applicant: John Gregory Ladas, Germantown, MD (US)

(72) Inventor: John Gregory Ladas, Germantown, MD (US)

( * ) Notice: Subject to any disclaimer, the term of this patent is extended or adjusted under 35 U.S.C. 154(b) by 0 days.

(21) Appl. No.: 18/396,349

(22) Filed: Dec. 26, 2023

(65) Prior Publication Data

US 2024/0122698 A1    Apr. 18, 2024

Related U.S. Application Data

(63) Continuation of application No. 16/145,751, filed on Sep. 28, 2018, now Pat. No. 11,890,184.

(Continued)

(51) Int. Cl.
| | |
|---|---|
| *A61F 2/16* | (2006.01) |
| *A61B 3/00* | (2006.01) |
| *G02C 7/04* | (2006.01) |
| *G16H 20/40* | (2018.01) |
| *G16H 40/60* | (2018.01) |
| *G16H 50/50* | (2018.01) |
| *G16H 50/70* | (2018.01) |
| *A61B 34/10* | (2016.01) |

(52) U.S. Cl.
CPC .......... *A61F 2/1613* (2013.01); *A61B 3/0025* (2013.01); *A61F 2/1678* (2013.01); *G02C 7/049* (2013.01); *G16H 20/40* (2018.01); *G16H 40/60* (2018.01); *G16H 50/50* (2018.01); *G16H 50/70* (2018.01); *A61B 2034/108* (2016.02); *A61F 2/16* (2013.01); *A61F 2002/1681* (2013.01); *A61F 2240/002* (2013.01); *G02C 7/047* (2013.01)

(58) Field of Classification Search
CPC ........ A61F 2/1613; A61F 2/1678; A61F 2/16; A61F 2002/1681; A61F 2240/002; A61B 3/0025; A61B 2034/108; G02C 7/049; G02C 7/047; G16H 20/40; G16H 40/60; G16H 50/50; G16H 50/70
USPC ...................... 623/6.11; 351/159.74, 159.77
See application file for complete search history.

(56) References Cited

U.S. PATENT DOCUMENTS

| | | |
|---|---|---|
| 2008/0004610 A1 | 1/2008 | Miller et al. |
| 2012/0274895 A1 | 11/2012 | Van Der Mooren et al. |

(Continued)

*Primary Examiner* — William R Alexander
(74) *Attorney, Agent, or Firm* — ArentFox Schiff LLP

(57) ABSTRACT

Aspects of the present invention may include systems and methods for intraocular lens selection using a formula and a deep learning machine to estimate the error of the formula. In an aspect, the disclosure provides a method for intraocular lens selection. The method may include obtaining at least two ocular measurement parameters and a lens selection parameter for an eye. The method may include determining an intraocular lens power based on a formula using the at least two ocular measurement parameters. The method may include determining an estimated error of the formula using a deep learning machine trained on verified post-operative results using intraocular lenses selected by the formula. The method may include adjusting the lens selection parameter based on the estimated. The method may include redetermining the intraocular lens power based on the formula and the adjusted lens selection parameter.

33 Claims, 14 Drawing Sheets

Related U.S. Application Data

(60) Provisional application No. 62/566,021, filed on Sep. 29, 2017.

(56) References Cited

U.S. PATENT DOCUMENTS

| | | |
|---|---|---|
| 2012/0310337 A1 | 12/2012 | Hacker et al. |
| 2013/0050641 A1 | 2/2013 | Van Der Mooren et al. |
| 2015/0057989 A1 | 2/2015 | Hacker et al. |
| 2015/0103313 A1* | 4/2015 | Sarver .................. A61B 3/1015 |
| | | 351/205 |
| 2017/0316571 A1 | 11/2017 | Martínez-Enríquez et al. |
| 2018/0035883 A1 | 2/2018 | Kumar et al. |
| 2019/0209242 A1* | 7/2019 | Padrick .................. G06N 20/00 |
| 2020/0229870 A1* | 7/2020 | Sarangapani .......... A61B 3/117 |
| 2021/0106385 A1* | 4/2021 | Bhattacharya ............ G06T 7/70 |
| 2023/0248437 A1 | 8/2023 | Padrick et al. |

* cited by examiner

FIG. 5

LADAS SUPER FORMULA | Toric Calculator | Post-LASIK Calulator | Settings | Log out Right (OD) — 510

Left (OS) — 520

MEASUREMENTS:
Axial Length: 511
K1: 512
K2: 513
K: Index: 514
Axial Length: 515
LENS SELECTION:
A-Constant: 516
Target Retraction: 517

Surgeon
530
531
532

Import Patient
Plot
Reset

500

SYSTEMS, APPARATUSES, AND METHODS FOR INTRAOCULAR LENS SELECTION USING ARTIFICIAL INTELLIGENCE

CLAIM OF PRIORITY UNDER 35 U.S.C. § 119

This application is a continuation of U.S. patent application Ser. No. 16/145,751, titled "SYSTEMS, APPARATUSES, AND METHODS FOR INTRAOCULAR LENS SELECTION USING ARTIFICIAL INTELLIGENCE" filed Sep. 28, 2018, which claims priority to U.S. Provisional Application No. 62/566,021, titled "SYSTEMS, APPARATUSES, AND METHODS FOR INTRAOCULAR LENS SELECTION USING THREE-DIMENSIONAL SUPER SURFACE" filed Sep. 29, 2017, which is assigned to the assignee hereof, and incorporated herein by reference in its entirety.

FIELD OF THE INVENTION

Aspects of the present invention relate to systems, apparatuses, and methods for selecting an intraocular lens.

BACKGROUND

Multiple intra-ocular lens (IOL) calculation formulas are currently available. For example, the SRK I formula 13 may be considered a first-generation formula. More recent third-generation formulas such as the SRK/T formula add theoretical portions to the formula in order to improve its accuracy, which increases the complexity of the formula when compared to the SRK I formula. Additional IOL calculation formulas include the Hoffer Q, Holladay I, Haigis, and SRK/T formulas. The Koch adjustment may also be used to adjust any of these formulas. Although the existing formulas give similar results over a range of input parameters, they also diverge significantly at specified ranges of input parameters Individual formulas have been demonstrated to work best with certain input parameters. The input parameters may include ocular measurement parameters such as axial length, corneal power, a white-to-white distance, gender or sex, anterior chamber depth, pre-operative refraction, and/or lens thickness. In an aspect, at least two ocular measurement parameters may be used. In an aspect, the at least two parameters may include axial length and corneal power. For example, a particular formula may work better with "shorter" eyes and another particular formula may work better in "longer" eyes. Further, "adjustments" to these formulas may be used to obtain better results. An "adjustment" may include any additional factor applied to an IOL calculation formula.

The current state of the art includes selecting one formula to determine the lens power and possibly comparing the results to those obtained using another formula. A limited number of ophthalmologists understand the data and literature that support using one formula over another. While the use of a particular formula may be debatable, there are certain scenarios (e.g. a specific measured axial length or corneal power) in which one formula is generally accepted as better than others.

SUMMARY

Aspects of the present disclosure may include systems and methods, apparatuses for intraocular lens selection using a lens selection formula and a neural network to estimate an error of the lens selection formula. In an aspect, the lens selection formula may utilize a three dimensional super surface. The super surface may represent portions of a plurality of lens selection formulas based on a range of measurements most suitable to each individual intraocular lens selection formula.

In an aspect, the disclosure provides a method for intraocular lens selection and/or apparatuses and systems therefor. The method may include obtaining at least two ocular measurement parameters and a lens selection parameter for an eye. The method may include determining an intraocular lens power based on a formula using the at least two ocular measurement parameters. The method may include determining an estimated error of the formula using a neural network trained on verified post-operative results including post-operative refractions corresponding to intraocular lens powers. The method may include adjusting the lens selection parameter based on the estimated error. The method may include redetermining the intraocular lens power based on the formula and the adjusted lens selection parameter.

In an aspect, determining the intraocular lens power based on the formula may include determining a relevant portion of a super surface including ideal or near ideal portions of a plurality of intraocular lens selection formulas based on a range of the at least two ocular measurement parameters most suitable to each individual intraocular lens selection formula.

In an aspect, the method may further include rendering the super surface, including the relevant portion thereof, such as on a monitor or other display device, or other suitable presentation medium. Rendering the super surface may include rendering the super surface includes rendering a variation from the super surface determined by the neural network. In another aspect, the method may include determining a divergence between each intraocular lens selection formula for the at least two ocular measurement parameters. The plurality of intraocular lens selection formulas may include at least two of the following formulas: a Hoffer Q formula, a Holladay I formula, a Haigis formula, a SRK/T formula and/or adjustments thereto. The lens selection parameter may be one of a target refraction or A-constant. The at least two ocular measurement parameters may include: axial length, corneal power, corneal power index, and anterior chamber depth. The ocular measurement parameters may also include post-refractive measurement (e.g., due to previous operations). In an aspect, other factors that have been shown to affect IOL selection or performance may be included.

In another aspect, the disclosure provides an apparatus for intraocular lens selection. The apparatus may include an ocular measurement device configured to measure at least two ocular measurement parameters. For example, the ocular measurement device may measure an axial length and a corneal power of an eye. The apparatus may further include a memory and a processor communicatively coupled with the ocular measurement device and the memory. The processor and memory may be configured to obtain at least two ocular measurement parameters and a lens selection parameter for an eye. The processor and memory may be configured to determine an intraocular lens power based on a formula using the at least two ocular measurement parameters. The processor and memory may be configured to determine an estimated error of the formula using a neural network trained on verified post-operative results including post-operative refractions corresponding to intraocular lens powers. The processor and memory may be configured to adjust the lens selection parameter based on the estimated error. The processor and memory may be configured to redetermine the intraocular lens power based on the formula and the adjusted lens selection parameter.

In an aspect, the apparatus may further include a monitor and/or other display device and/or other user interaction features, wherein the processor is configured to render the super surface including the relevant portion thereon. In an aspect, the ocular measurement device may be one of an ultrasound device or an optical biometer.

In another aspect, the disclosure provides a non-transitory computer-readable medium storing computer executable instructions. The instructions may cause a computer to receive at least two ocular measurement parameters, such as from a measurement device; determine an intraocular lens power based on a formula using the at least two ocular measurement parameters; determine an estimated error of the formula using a neural network trained on verified post-operative results including post-operative refractions corresponding to intraocular lens powers; adjust the lens selection parameter based on the estimated error; and redetermine the intraocular lens power based on the formula and the adjusted lens selection parameter.

Additional advantages and novel features relating to aspects of the present invention will be set forth in part in the description that follows, and in part will become more apparent to those skilled in the art upon examination of the following or upon learning by practice thereof.

BRIEF DESCRIPTION OF THE FIGURES

In the drawings:

FIG. 5 illustrates an example input user interface for use in accordance with aspects of the present disclosure.

DETAILED DESCRIPTION

Aspects of the present disclosure may include systems, apparatuses, and methods for intraocular lens selection using a three dimensional super surface. The super surface may represent portions of a plurality of lens selection formulas based on a range of measurements most suitable to each individual intraocular lens selection formula.

The disclosure provides a novel intraocular lens calculation formula based on a combination of existing intraocular lens (IOL) calculation formulas using graphical analysis to determine the range of input parameters, such as portions thereof over which existing IOL calculation formulas are most accurate. These individual formulas have never been presented or thought of as 3 dimensional objects that may be combined and overlapped according to a set of determined "criteria". The intraocular lens calculation formula will graphically "pick and choose" the parts of each formula that have either been proven or are believed to be the most accurate and combine this into one overall formula. This combined or "super" formula may be adjusted and/or optimized further (e.g., iteratively) as other formulas are proposed or additional data becomes available.

Figure 1A:
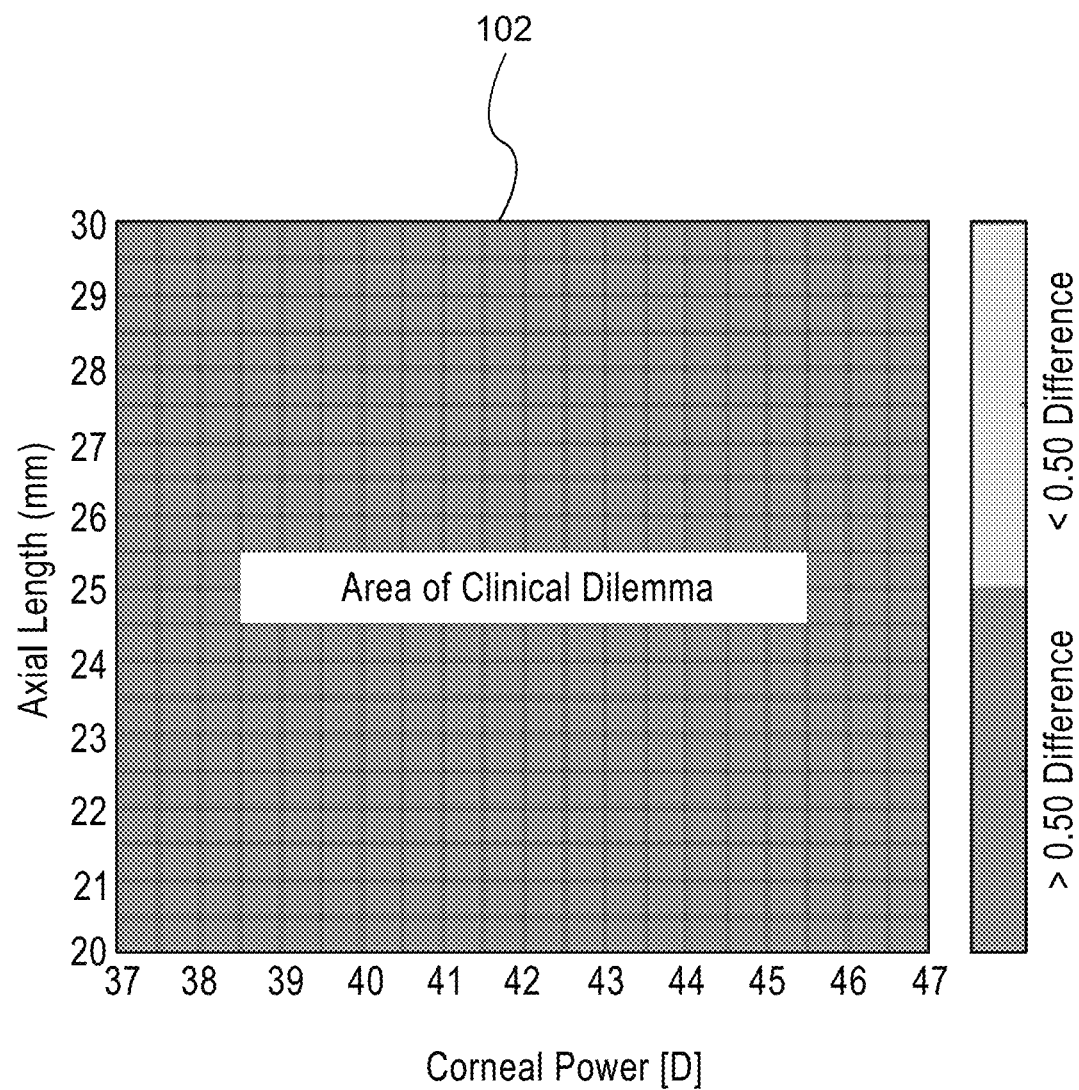
FIGS. 1A-1C illustrate a graphical representation of regions of ocular measurements where existing formulas differ and represent a clinical dilemma.
Figure 1B:
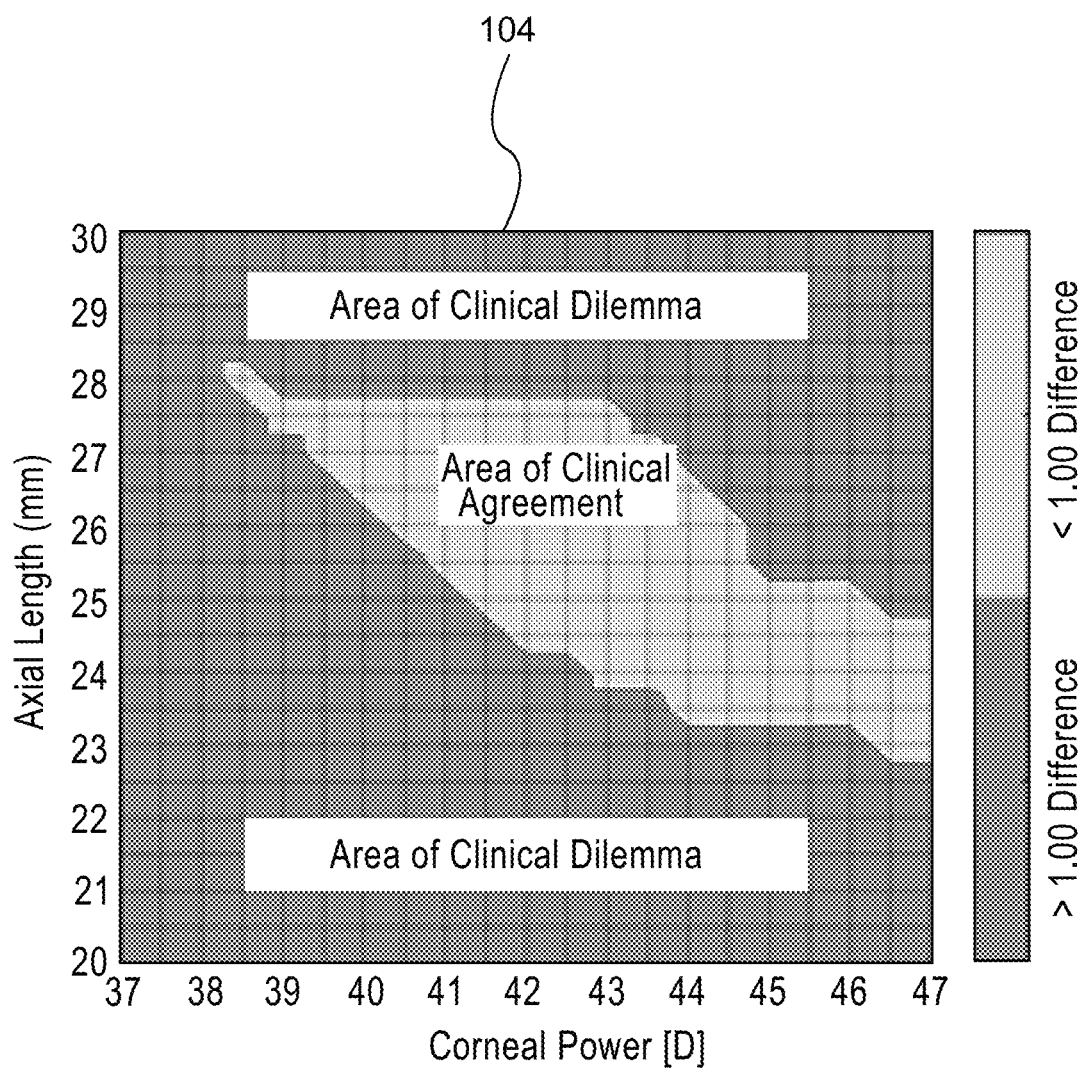
Figure 1C:
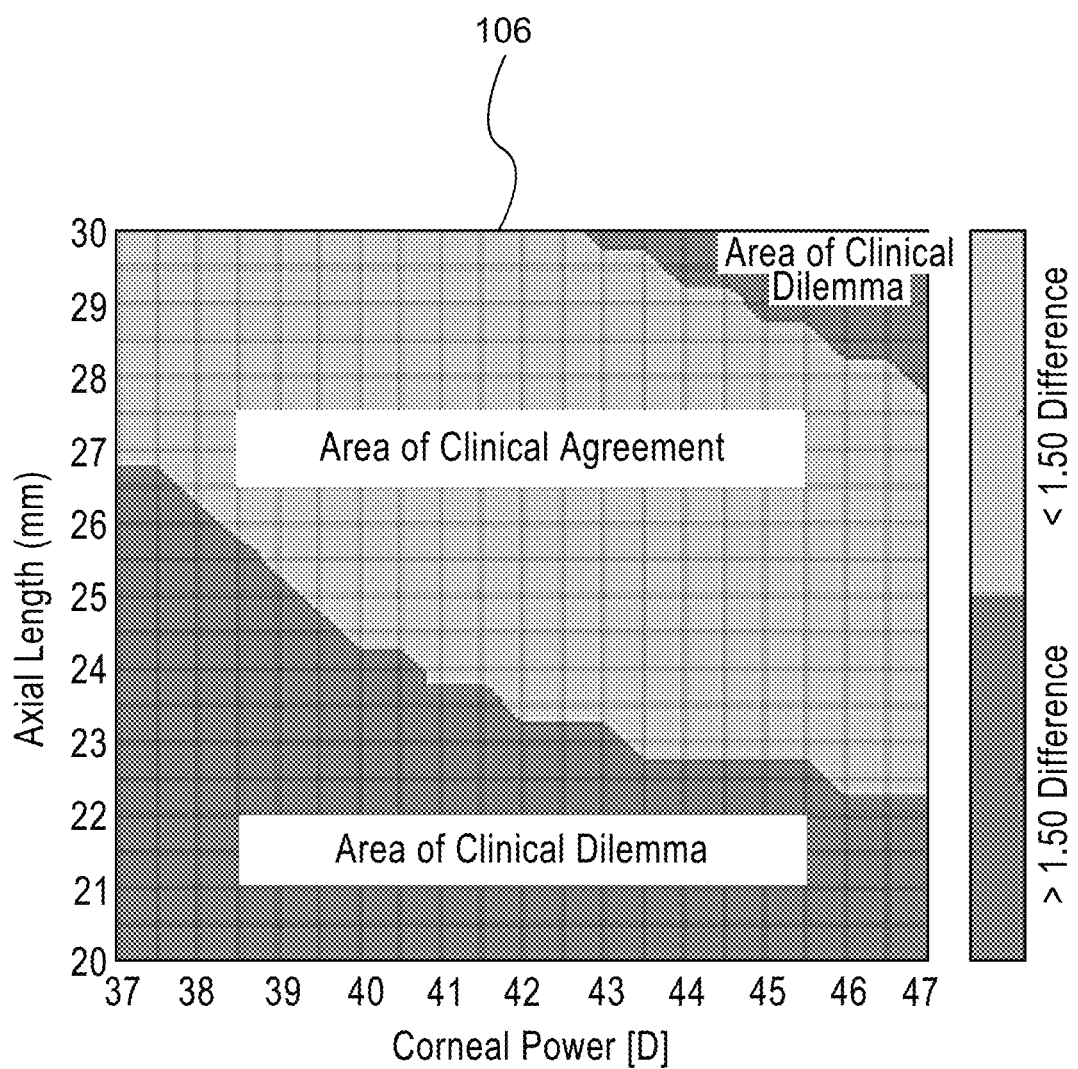

FIGS. 1A-1C shows Ladas-Siddiqui graphs, which highlight areas of clinical agreement and disparity between formulas at specified ranges of corneal power and axial length. Graph 102 (FIG. 1A) demonstrates that all formulas differ from at least one of the other four by greater than 0.5 diopter over the entire range of input parameters. As seen in graph 104 (FIG. 1B), when the tolerance for divergence between formulas is increased to 1.0 diopter in predicted IOL power (a clinically undesirable level), there are areas of correspondence between all formulas tested. The areas of correspondence increase further when tolerance is raised to 1.5 diopters as shown in graph 106 (FIG. 1C). Thus, resolving these areas of discrepancy is of high clinical relevance and requires not only access to each formula but also a detailed knowledge of their particular strengths and weaknesses. Depicting comparisons between IOL formulas in this manner shows the specific range of input parameters over which the formulas diverge, enabling more precise understanding of the differences between formulas.

Figure 2A:
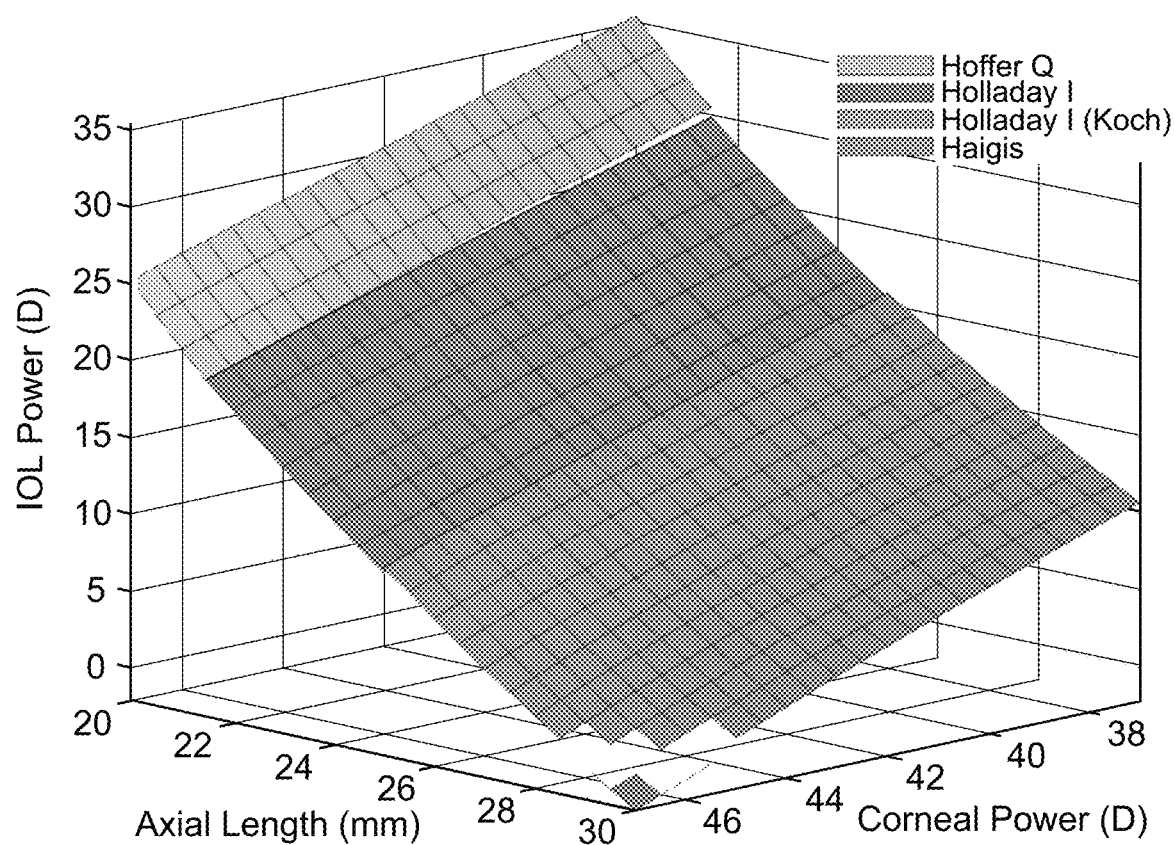
FIGS. 2A-2C illustrate three-dimensional surfaces including ideal or near ideal portions of a plurality of intraocular lens selection formulas, for use in accordance with aspects of the present disclosure.
Figure 2B:
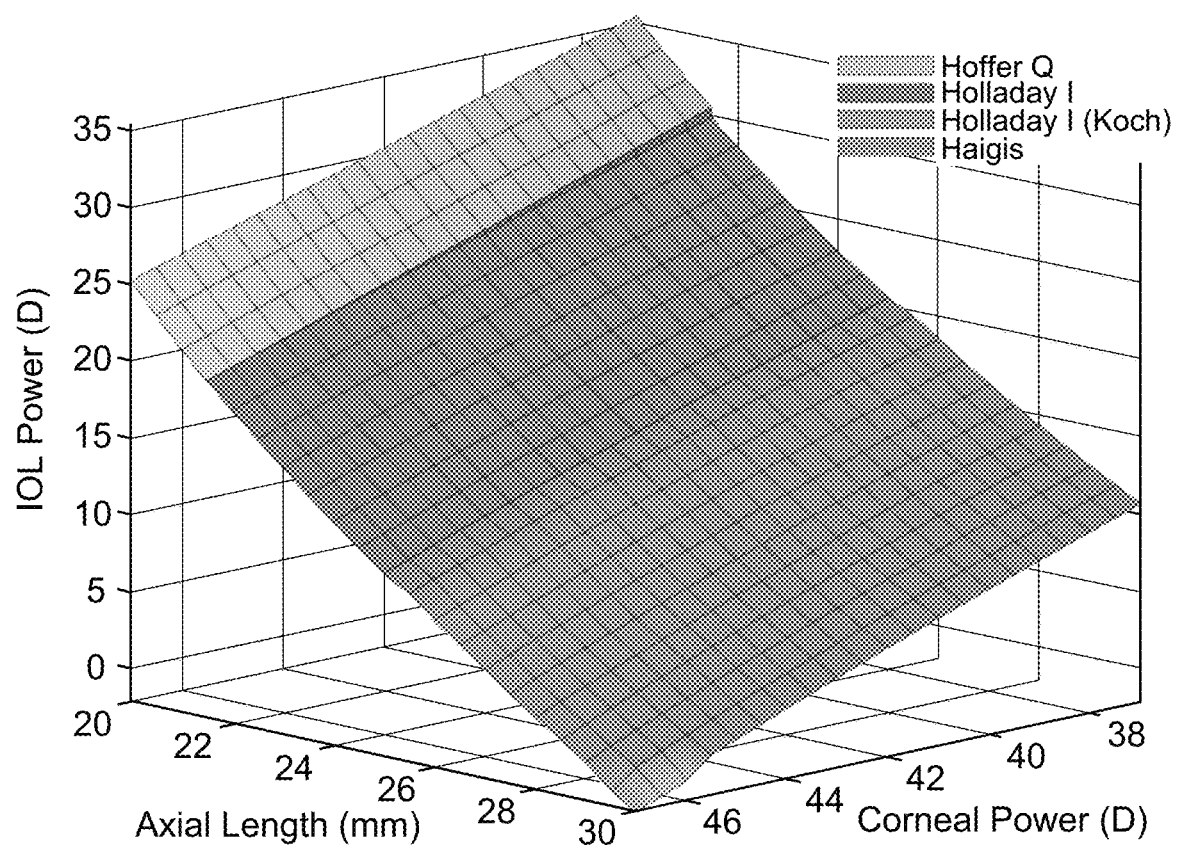
Figure 2C:
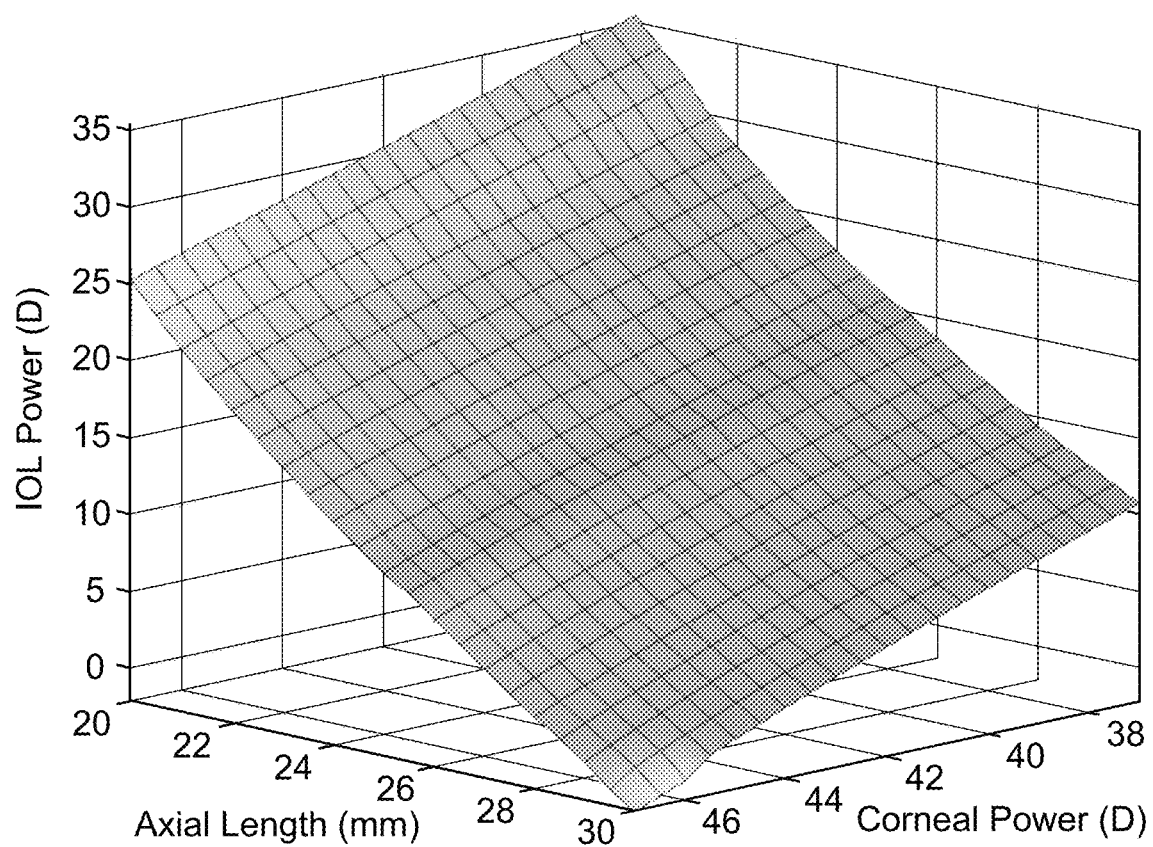

FIGS. 2A-C graphically illustrate a combined super formula based on the strengths and weaknesses of each IOL formula. The super formula combines the ideal, most accurate output portions of each IOL formula into a combined super formula. FIGS. 2A-C illustrate the graphical results of this super formula, showing a step-wise development and evolution of a singular multi-faceted surface including the most accurate portions of multiple individual formulas based on specified ranges of input variables. FIG. 2A is a graph showing regions where different IOL selection formulas are determined to be optimal. FIG. 2B is a graph showing interconnection among the regions for the different IOL selection formulas. FIG. 2C shows a surface for a combined super formula. In an aspect, although a surface is illustrated to represent the output of formulas using two ocular measurements, an IOL selection formula or system may use more than two ocular measurements. An IOL selection system or formula having multiple inputs may be conceived of as a multi-dimensional hyper-surface.

Another technique for determining an intraocular lens involves use of machine learning. For example, a neural network may be trained using the results of previous operations. The neural network may then be provided with the pre-operative measurements of a patient. The neural network will attempt to classify the patient's pre-operative measurements against the training set to determine the lens power. This approach may be limited based on the training data, and some sets of pre-operative measurements may be considered out-of-bounds and the neural network may be unable to produce a result. Moreover, the neural network may potentially produce anomalous results due to random correlations in the training data. Further, changes to the training data may require retraining the neural network.

This disclosure describes methods, apparatuses, and systems for combining and using any number of multiple formulas into a single formula using the ideal parts of each constituent formula based, for example, on theoretical and/or empirical information. Further, this disclosure describes a technique for improving a formula based approach using a combination of a formula and machine learning. For example, in an aspect, a neural network may be trained to determine an estimated error that may result from using a calculated intraocular lens power. The estimated error may be used to adjust a lens selection parameter such as target refraction or A-constant, and the formula may be used to recalculate the intraocular lens power using the adjusted lens selection parameter.

Figure 3:
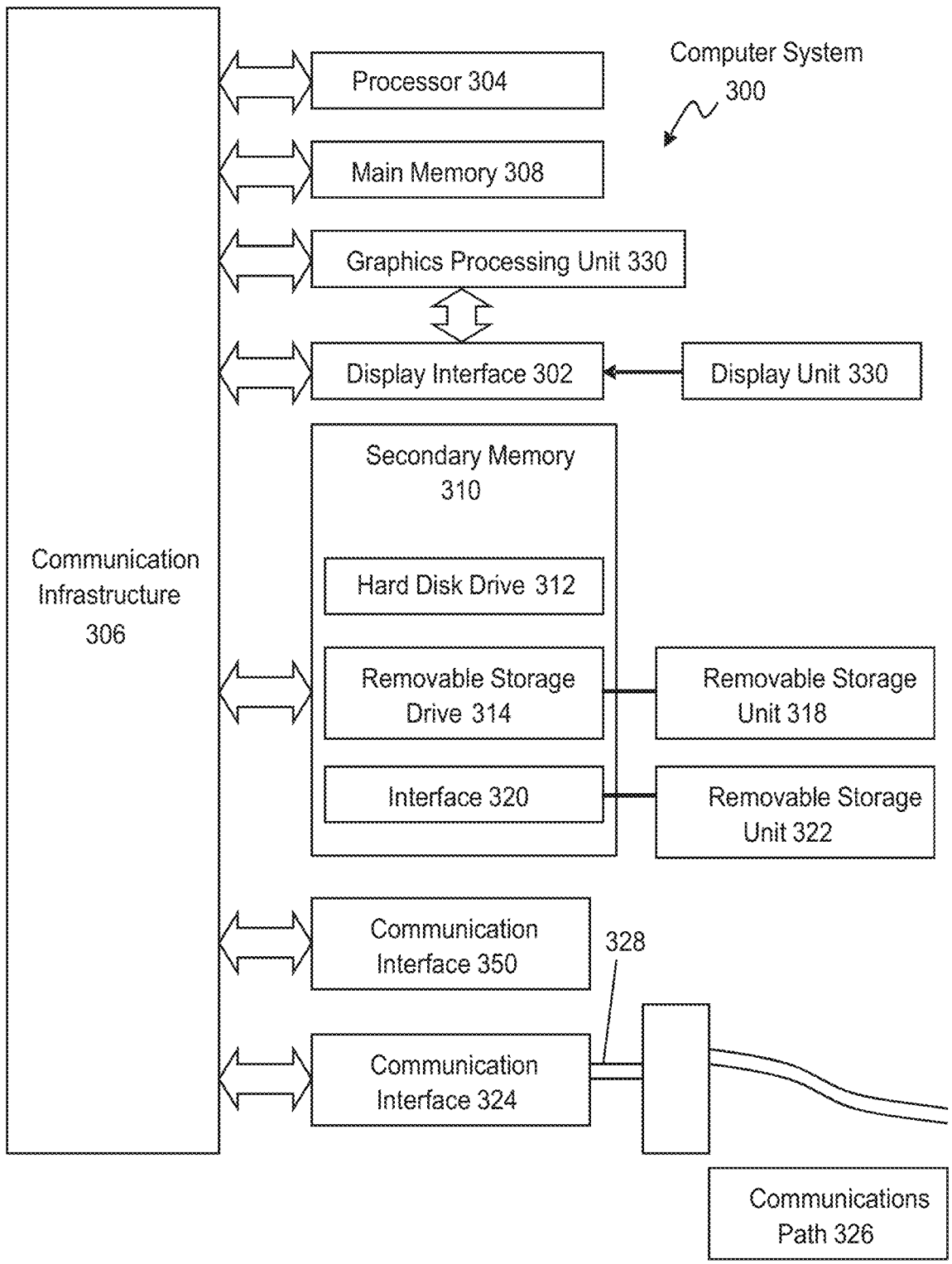
FIG. 3 illustrates various features of an example computer system for use in conjunction with aspects of the present disclosure.

Aspects of the present disclosure may be implemented using hardware, software, or a combination thereof and may be implemented in one or more computer systems or other processing systems. In an aspect of the present disclosure, features are directed toward one or more computer systems capable of carrying out the functionality described herein. An example of such a computer system 300 is shown in FIG. 3.

Computer system 300 includes one or more processors, such as processor 304. The processor 304 is connected to a communication infrastructure 306 (e.g., a communications bus, cross-over bar, or network). Various software aspects are described in terms of this example computer system. After reading this description, it will become apparent to a person skilled in the relevant art(s) how to implement aspects of the disclosure using other computer systems and/or architectures.

Computer system 300 can include a display interface 302 that forwards graphics, text, and other data from the communication infrastructure 306 (or from a frame buffer not shown) for display on a display unit 330. For example, the display interface 302 may forward a graphical rendering of a super surface from the processor 304 to the display unit 330. Computer system 300 also includes a main memory 308, preferably random access memory (RAM), and may also include a secondary memory 310. The secondary memory 310 may include, for example, a hard disk drive 312 and/or a removable storage drive 314, representing a floppy disk drive, a magnetic tape drive, an optical disk drive, a universal serial bus (USB) flash drive, etc. The removable storage drive 314 reads from and/or writes to a removable storage unit 318 in a well-known manner. Removable storage unit 318 represents a floppy disk, magnetic tape, optical disk, USB flash drive, etc., which is read by and written to removable storage drive 314. As will be appreciated, the removable storage unit 318 includes a computer usable storage medium having stored therein computer software and/or data.

Alternative aspects of the present disclosure may include secondary memory 310 and may include other similar devices for allowing computer programs or other instructions to be loaded into computer system 300. Such devices may include, for example, a removable storage unit 322 and an interface 320. Examples of such may include a program cartridge and cartridge interface (such as that found in video game devices), a removable memory chip (such as an erasable programmable read only memory (EPROM), or programmable read only memory (PROM)) and associated socket, and other removable storage units 322 and interfaces 320, which allow software and data to be transferred from the removable storage unit 322 to computer system 300.

Computer system 300 may also include a communications interface 324. Communications interface 324 allows software and data to be transferred between computer system 300 and external devices. Examples of communications interface 324 may include a modem, a network interface (such as an Ethernet card), a communications port, a Personal Computer Memory Card International Association (PCMCIA) slot and card, etc. Software and data transferred via communications interface 324 are in the form of signals 328, which may be electronic, electromagnetic, optical or other signals capable of being received by communications interface 324. These signals 328 are provided to communications interface 324 via a communications path (e.g., channel) 326. This path 326 carries signals 328 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 380, a hard disk installed in hard disk drive 370, and signals 328. These computer program products provide software to the computer system 300. Aspects of the present disclosure are directed to such computer program products.

In an aspect, the computer system 300 may include an ocular measurement device 350. The ocular measurement device 350 may determine one or more ocular measurement parameters. An ocular measurement device may include any device for measuring an eye. For example, the ocular measurement device 350 may measure an axial length and a corneal power of an eye. In an aspect, the ocular measurement device 350 may further measure a white-to-white distance, anterior chamber depth, pre-operative refraction, and/or lens thickness. The ocular measurement device 350 may further receive input of ocular measurement parameters (e.g., gender or sex). The axial length may be a distance from the surface of the cornea to the retina. The corneal power may be a dioptric power of the cornea. As another example, the ocular measurement device 350 may measure an anterior chamber depth of an eye. In an aspect, the ocular measurement device 350 may be an ultrasound device. In another aspect, the ocular measurement device 350 may be an optical biometer. Various optical biometers are available under the names WAVELIGHT®, LENSTAR®, and IOL MASTER. In another aspect, the ocular measurement device 350 may include an intraoperative abberrometry device. The intraoperative abberrometry device may take measurements of refractive properties of the eye during surgery. For example, an intraoperative abberrometry device may provide information on sphere, cylinder, and axis of the eye. Additionally, an ocular measurement device may include a post-operative measurement device such as a wavefront analyzer. The ocular measurement device 350 may be communicatively coupled to the processor 304 via the communication infrastructure 306, the communications interface 324, and/or the communications path 326.

Computer programs (also referred to as computer control logic) are stored in main memory 308 and/or secondary memory 310. Computer programs may also be received via communications interface 324. Such computer programs, when executed, enable the computer system 300 to perform the features in accordance with aspects of the present disclosure, as discussed herein. In particular, the computer programs, when executed, enable the processor 304 to perform the features in accordance with aspects of the present disclosure. Accordingly, such computer programs represent controllers of the computer system 300.

In an aspect of the present disclosure where the disclosure is implemented using software, the software may be stored in a computer program product and loaded into computer system 300 using removable storage drive 314, hard drive 312, or communications interface 320. The control logic (software), when executed by the processor 304, causes the processor 304 to perform the functions described herein. In another aspect of the present disclosure, the system is implemented primarily in hardware using, for example, hardware components, such as application specific integrated circuits (ASICs). Implementation of the hardware state machine so as to perform the functions described herein will be apparent to persons skilled in the relevant art(s).

In yet another aspect of the present disclosure, the disclosure may be implemented using a combination of both hardware and software.

Figure 4:
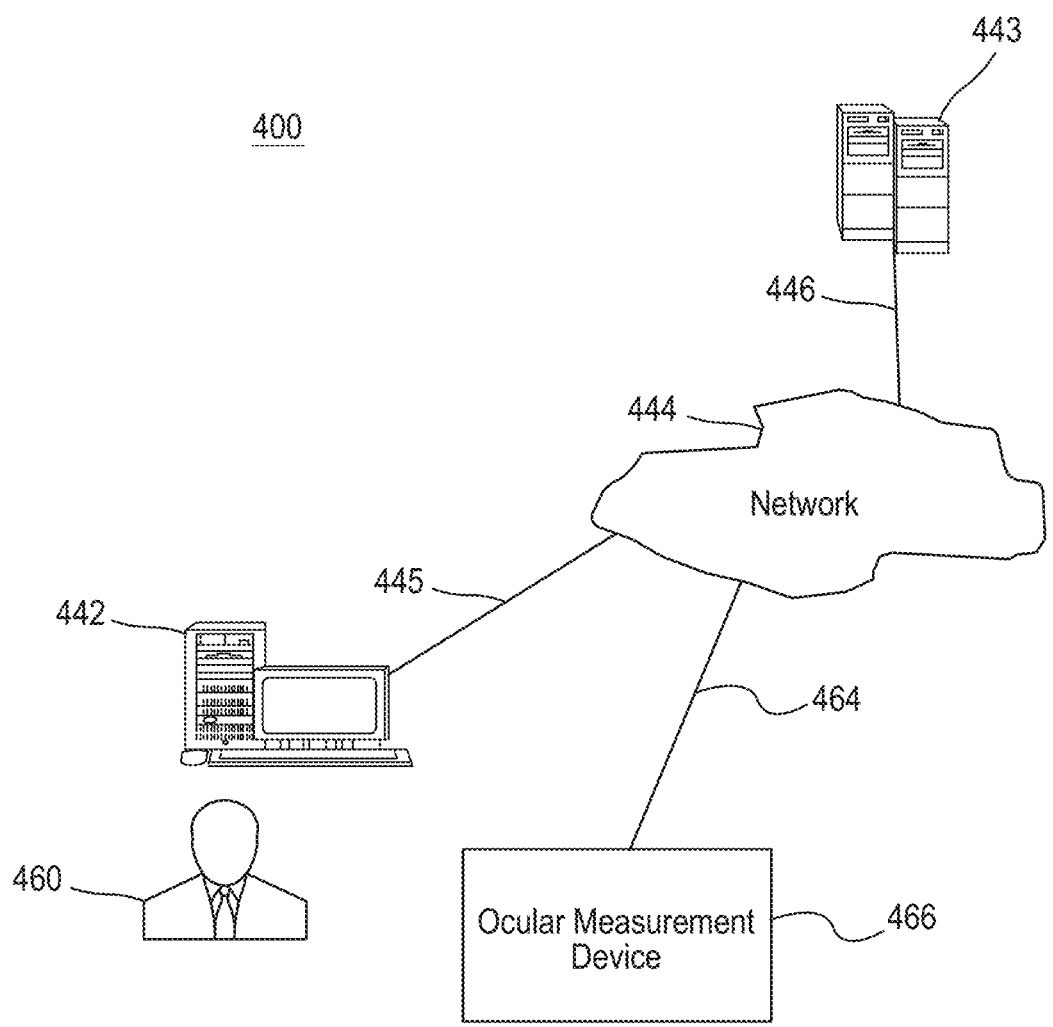
FIG. 4 illustrates an example system diagram of various hardware components and other features for use in accordance with aspects of the present disclosure.

FIG. 4 shows a communication system 400 usable in accordance with aspects of the present disclosure. The communication system 400 includes one or more accessors 460 (also referred to interchangeably herein as one or more "users") and one or more terminals 442 and/or other input device or devices (e.g., an ocular measurement device 466). In an aspect, the ocular measurement device 466 may be similar to the ocular measurement device 350 (FIG. 3). The ocular measurement device 466 may further be configured to communicate with the network 444. In one aspect of the present disclosure, data for use is, for example, input and/or accessed after being received from an input device by accessors 460 via terminals 442, such as personal computers (PCs), minicomputers, mainframe computers, microcomputers, telephonic devices, or wireless devices, personal digital assistants ("PDAs") or a hand-held wireless devices (e.g., wireless telephones) coupled to a server 443, such as a PC, minicomputer, mainframe computer, microcomputer, or other device having a processor and a repository for data and/or connection to a repository for data, via, for example, a network 444, such as the Internet or an intranet, and/or a wireless network, and couplings 445, 446, 464. The couplings 445, 446, 464 include, for example, wired, wireless, or fiberoptic links. In another aspect of the present disclosure, the method and system of the present disclosure may include one or more features that operate in a stand-alone environment, such as on a single terminal.

In an aspect, the server 443 may be an example of the computer system 300 (FIG. 3). In an aspect, for example, the server 443 may be configured to perform the methods described herein. For example, the server 443 may obtain measurements such as an axial length and corneal power measurements from a terminal 442 and/or other input device. The measurements may be entered by an accessor 460, or provided by an ocular measurement device 350 (FIG. 3). The server 443 may determine a relevant portion of a super surface including ideal portions of a plurality of intraocular lens selection formulas based on a range of the axial length and corneal power measurements most suitable to each individual intraocular lens selection formula. Further, the server 443 may determine an intraocular lens power based on a formula for the relevant portion of the super surface.

FIG. 5 illustrates an example input user interface (UI) 500 for use in accordance with aspects of the present invention. The user interface 500 may be implemented by the server 443 and displayed on the terminal 442, for example. The user interface 500 may allow a user to enter pre-operative measurements of one or more eyes as well as target parameters. The user interface 500 allows simultaneous calculation and plotting of both eyes. Input-data may include the keratometry (K1, K2, and K Index), axial length, corneal index and anterior chamber depth (ACD). The K1 and K2 values may be averages of refractive power of the front surface of the eye including different angles. The K-index may be a standard refractive index for the cornea. Slight variations of the K-index may be used by different surgeons or in different countries. The anterior chamber depth is a measurement of the position of the original lens prior to removal. The lens A-constant and desired postop refraction are then selected and the optimized calculations are then performed. The lens A-constant is a property of a lens that may be specified by a manufacturer and may contribute to total refraction. The target refraction may be a goal specified by the surgeon. For example, a target refraction of 0.0 may be used.

The user interface 500 may include an input field 510 for a right eye and an input field 520 for a left eye. Each input field 510,520 may include input fields for specific measurements or parameters. For example, the input field 510 may include an axial length field 511, a K1 field 512, a K2 field 513, a K Index field 514, and an Optical ACD field 515. The input field 510 may also include lens selection parameters including an A-constant field 516 and a target refraction 517. The input fields 510, 520 may also include a help icon (e.g., "?") that provides a description of the measurement or parameter including allowed ranges. Some fields such as the K Index field 514 may use a drop-down menu to select a value. Additional fields that may be included in the user interface 500 include intraoperative aberrometry measurements such as sphere, cylinder, and axis of the eye.

Additionally, the user interface 500 may include a surgeon field 530, a patient field 531, and a patient ID field 532. The server 443 may generate records for the surgeon and patent based on the fields 530, 531, 532. The user interface 500 may also include an import option 540 that may allow a user to upload a file (e.g., a spreadsheet) including measurements and parameters for one or more patients. A dedicated toric calculator and a post-LASIK calculator may also be included.

Figure 6:
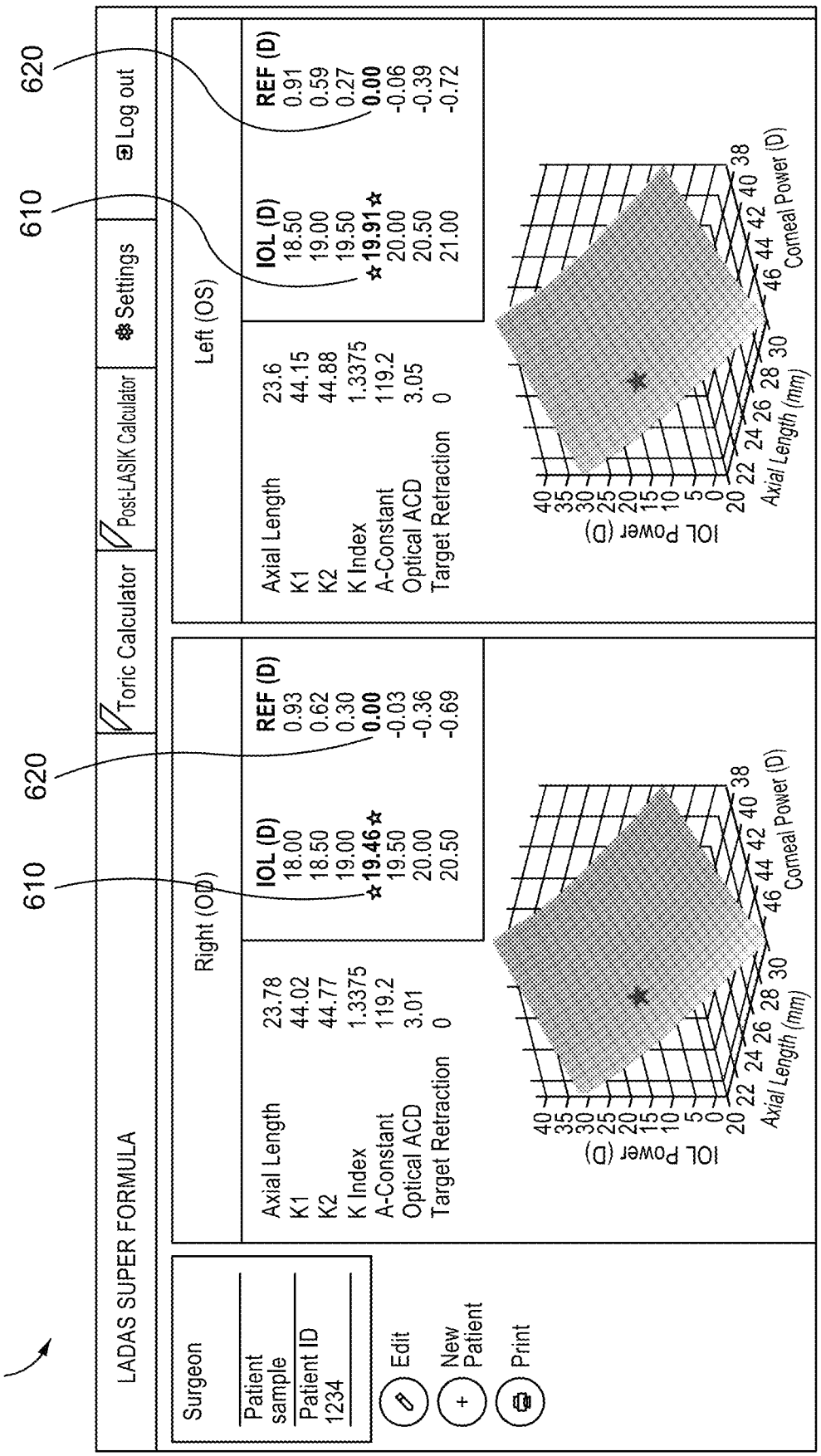
FIG. 6 illustrates an example output user interface for use in accordance with aspects of the present disclosure.

FIG. 6 illustrates an example output user interface 600 for use in accordance with aspects of the present invention. The user interface 600 may display a recommended intraocular lens power (IOL) 610. The user interface 600 may display multiple IOL power values corresponding to available lenses. The user interface 600 may also display an estimated final refraction (REF) 620 associated with each IOL power value. Additionally, the user interface 600 may include a graphical representation 630 of a supersurface used to select the intraocular lens power. The relevant point on the supersurface based on the measurements may be indicated. The inclusion of the three-dimensional graph is useful for a surgeon to know instantly if his patient has typical or unusual eyes. The user interface 600 may include output fields for each eye.

Figure 7:
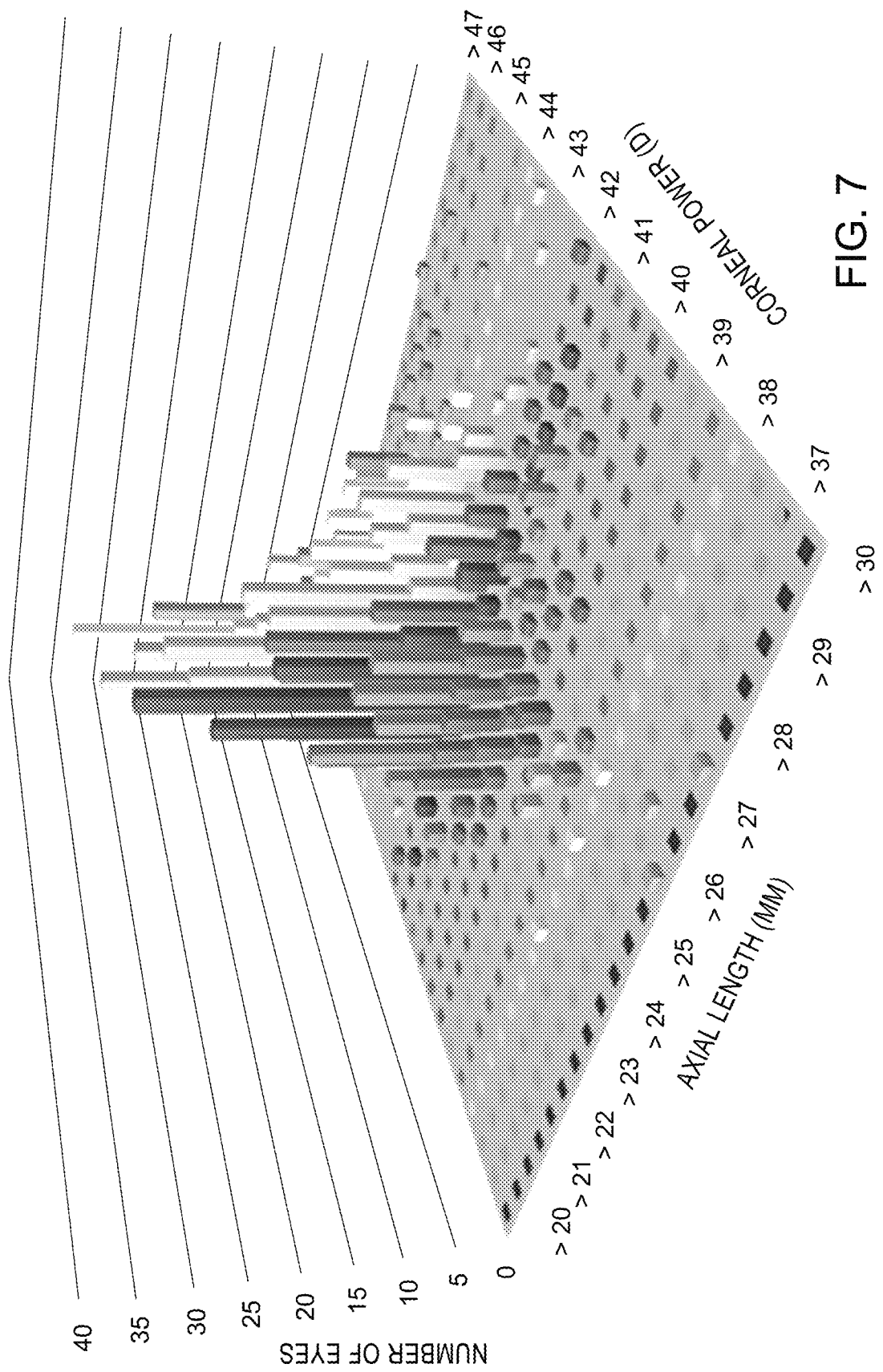
FIG. 7 illustrates a graph representing a data set of example eyes.

FIG. 7 illustrates a graph 700 representing a data set of example eyes. The data set may be collected from one or more surgeons. As illustrated, while most eyes have an average keratometry and axial length, there are also outliers.

Figure 8:
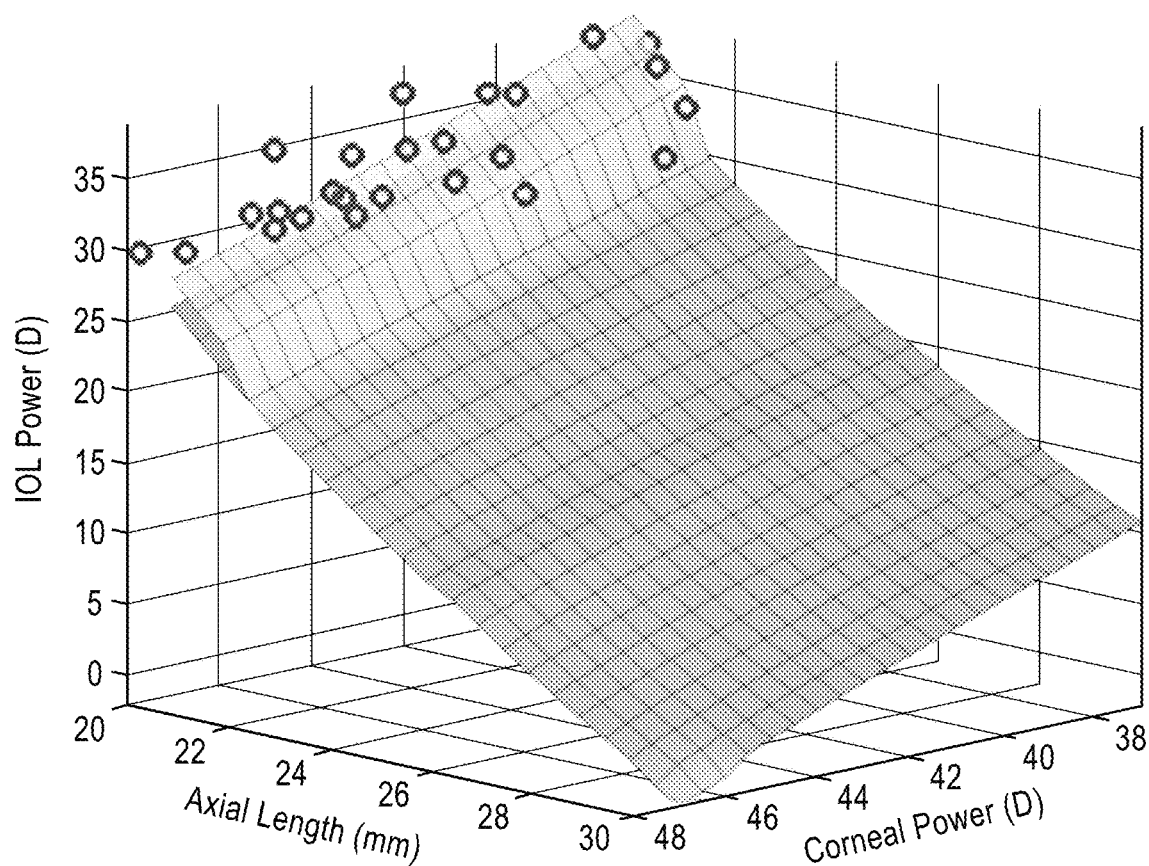
FIG. 8 illustrates a three-dimensional surface representative of a learned variation of a formula in accordance with aspects of the present disclosure.

FIG. 8 illustrates a three-dimensional surface representative of a learned variation of a formula. The original Ladas super surface has evolved to enhance accuracy for eyes of all dimensions including types of eyes previously though to present difficulties such as small eyes with short axial lengths. The circles represent data points of actual postop results that allow creation of an optimized Super Surface 810 compared with the original super surface 820, which is mostly overlapped by the new surface).

Figure 9:
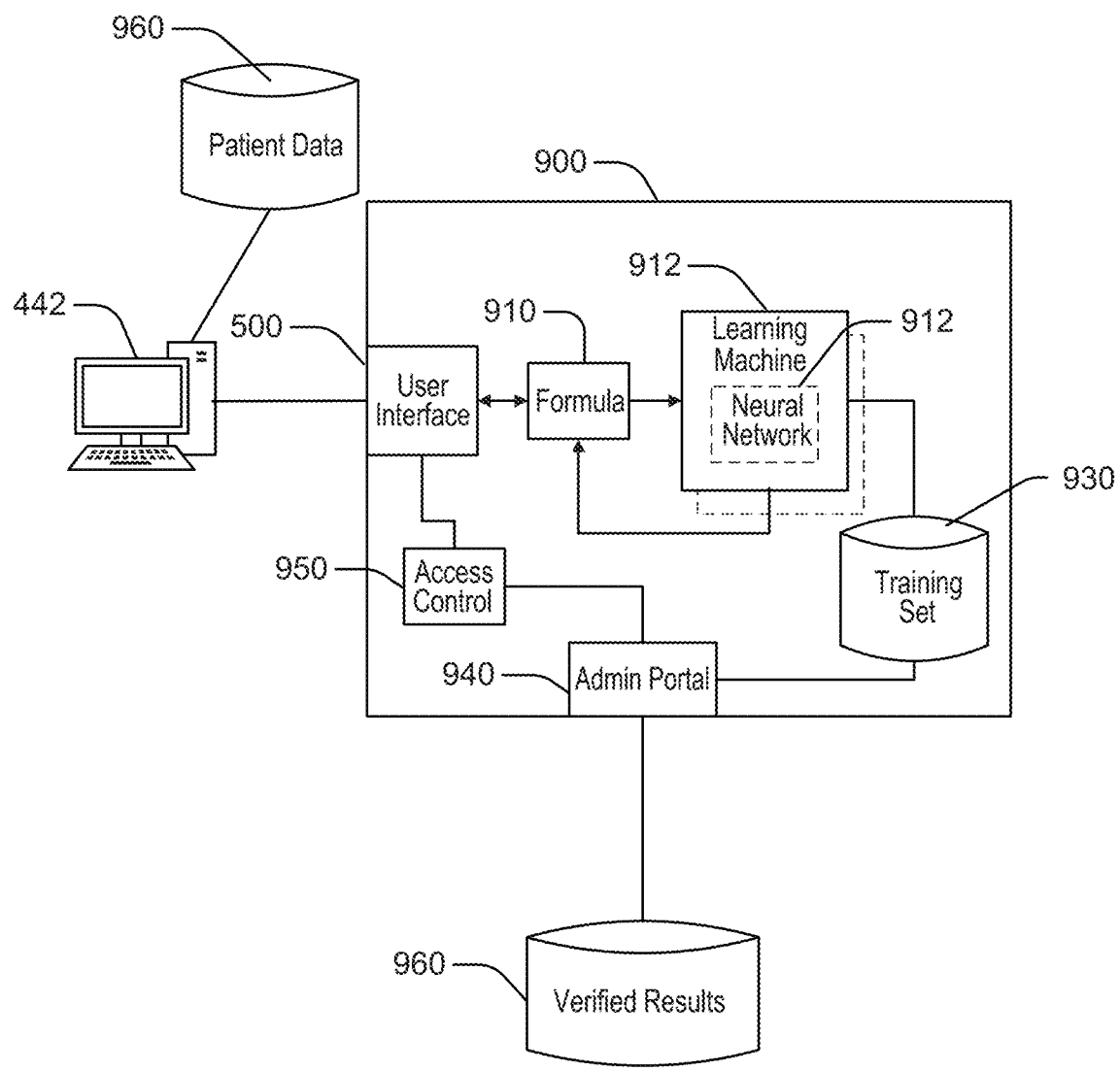
FIG. 9 is a diagram of an example computer system according to an aspect of the present disclosure.

In an aspect, the super surface or another formula may be customized to one or more surgeons. For example, verified results from a surgeon may be analyzed against the super surface or the formula to determine whether any patterns in the surgeon's operations can be detected. Turning now to FIG. 9, an example system 900 may recommend an intraocular lens power based on a formula and a trained deep learning machine 912.

The system 900 may be implemented on a server 443, for example. The system 900 may communicate with one or more terminals 442 via the user interfaces 500, 600 discussed above. The system 900 may include a formula component 910 for determining an intraocular lens power based on a formula using at least two ocular measurement parameters, a deep learning machine 912 such as neural network 920 for determining an estimated error of the formula, and the user interface 500 for obtaining at least two ocular measurement parameters and a target refraction or A-constant for an eye. The formula component 910 may further adjust the target refraction of A-constant based on the estimated error and redetermine the intraocular lens power based on the formula and the adjusted target refraction or A-constant. The system 900 may further include one or more training sets 930. The training sets 930 may include sets of post-operative data including two or more of the pre-operative measurements and parameters (e.g., axial length field 511, a K1 field 512, a K2 field 513, a K Index field 514, an Optical ACD field 515 and intraoperative aberrometry measurements such as sphere, cylinder, and axis of the eye), a selected intraocular lens power, and one or more lens selection parameters (e.g., post-operative refraction or A-constant). The training sets 930 may be used to train one or more of the deep learning machine 912 for estimating an error of an intraocular lens power determined by the formula 910, as explained in further detail below.

The system 900 may include an administrative portal 940 for controlling access to the system 900. For example, the administrative portal 940 may permit an administrative user to generate training sets 930 from verified results 960. The verified results 960 may be uploaded in the form of a database or spreadsheet. The administrative user may select combinations of measurements and parameters to use for the training sets 930. The administrative user may combine the uploaded verified results with any existing training sets 930. The system 900 may generate a new neural network 920 based on a new or updated training set 930. The system 900 may provide the administrative user with statistics regarding the neural network. For example, a neural network may be associated with input boundaries and correlation values. The administrative user may also configure access controls 950 to manage user accounts for different end users. The user accounts may be associated with saved patient data. Additionally, the user accounts may be associated with a customized neural network 920. For example, a customized neural network 920 may trained with verified results 960 exclusively from a particular surgeon, practice group, or lens manufacturer. A customized neural network 920 may help control for unknown or immeasurable factors affecting the particular surgeon, practice group, or lens manufacturer.

The formula component 910 may implement an intraocular lens power determination formula. An intraocular lens power determination formula may include any deterministic technique for generating an intraocular lens power based on two or more ocular measurements. For example, the formula component 910 may include software executed by a processor to determine an intraocular lens power according to a formula using input values from the user interface 500. For example, the formula component 910 may implement one or more of: a Hoffer Q formula, a Holladay I formula, a Haigis formula, a SRK/T formula, a Barrett Universal II or adjustments to any of these formulas. In an aspect, the formula component 910 may implement the Ladas Super Formula to select a calculation from one or more of the above formulas. For example, the formula component 910 may determine a relevant portion of a super surface including ideal or near ideal portions of a plurality of intraocular lens selection formulas based on a range of the axial length and corneal power measurements most suitable to each individual intraocular lens selection formula. The formula component 910 may provide the determined intraocular lens power value to the neural network 920 along with all of the input measurements and parameters. In an aspect, the formula component 910 may be implemented as a machine learned formula such as the Hill-RBF.

The learning machine 912 may use deep learning techniques to predict error of the formula component 910 based on the training set 930 including post-operative results. The learning machine 912 may be implemented by, for example, a neural network 920, which may utilize a Python based tensor flow. In an aspect, the learning machine 912 may include a computer processor (e.g., processor 304 that is programmed to execute instructions for developing the neural network 920 based on a network structure (e.g., number and type of layers). Once the learning machine 912 has trained the neural network 920 (or other learning machine), the processor configured with the trained learning machine 912 may determine the predicted error of the formula component 910 based the ocular measurement parameters. The neural network 920 may receive multiple numeric inputs to predict a single numeric output. In an implementation, the neural network may receive three numeric inputs (axial length, K, and ACD) and output an error value. The neural network 920 may be trained by one or more of the training set 930. The training sets 930 may be considered labelled data because the training sets 930 may include the post-operative refraction, which may be used to determine the accuracy or error of the formula. Accordingly, when the neural network 920 receives the set of numeric inputs, the neural network 920 may predict an estimated error of the formula component 910. The learning machine 912 may be implemented using different types of learning machines. For example, the learning machine 912 may use any combination of supervised and unsupervised learning techniques. The learning machine 912 may be structured as, for example, an artificial neural network, convolutional neural network, Bayesian network, or other deep learning model.

The formula component 910 may then adjust the formula inputs according to the predicted error. In particular, the formula component 910 may adjust a target refraction or an A-constant based on the predicted error. For example, the new target refraction may be set to the difference between the user input target refraction and the neural net predicted error. As a numeric example, for an eye with AL of 25, K of 45, and ACD of 3, the neural network 920 may predict an error of 0.25. That is, when the formula component 910 calculates an eye with AL of 25, K of 45, ACD of 3, and A constant of 119 (doesn't matter what user chooses for this) and target refraction of −0.5, then the eye will get re-calculated using the current formula component 910 but using the new target refraction value of −0.5−0.25=−0.75 instead of the user input target refraction. In other words, the formula component 910 may adjust one component of the formula's input (e.g., target refraction) by subtracting the neural network predicted error from the input value.

In an aspect, the formula component 910 may limit the adjustment to the formula by the neural network predicted error. For example, the neural network 920 may produce an extreme value in the case of an out-of-bounds case where the neural network 920 does not have good training data. The formula component 910 may limit the value of the predicted error. For example, the formula component 910 may limit the neural network predicted error never to exceed +/−0.5.

In an aspect, the neural network 920 may be adjusted based on a new ocular measurement. For example, in an implementation, the neural network 920 was provided with both pre-operative and post-refractive measurements of patients who had previously had laser-assisted in-situ keratomileusis (LASIK). The post-refractive measurements can be viewed as an error in the formula due to the previous refractive surgery. Being trained based on the difference for the pre-operative measurements and post-refractive measurements, the neural network 920 may provide a correction to the result provided by the IOL formula component 910.

Figure 10:
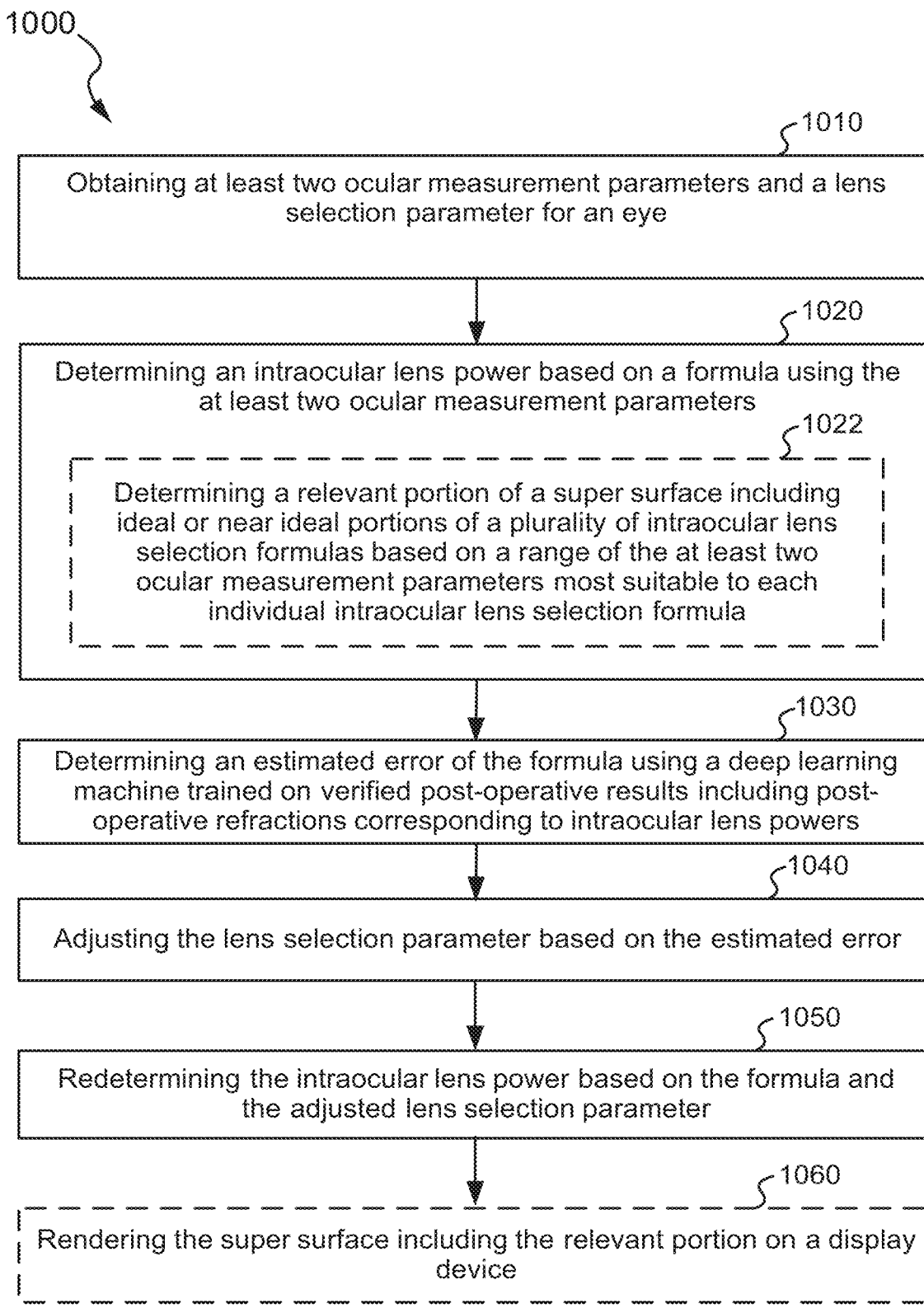
FIG. 10 is a flowchart of an example method for recommending an intraocular lens power according to an aspect of the disclosure.

FIG. 10 is a flowchart illustrating an example method 1000 of providing a recommended intraocular lens power. The method 1000 may be performed by the system 900.

In block 1010 the method 1000 includes obtaining at least two ocular measurement parameters and a lens selection parameter for an eye. In an aspect, for example, the UI 500 may obtain the at least two ocular measurement parameters and a lens selection parameter for an eye. In an implementation, the UI 500 may obtain the parameters for both eyes of a patient. In another implementation, the measurement parameters may be obtained from an ocular measurement device 466. The ocular measurement parameters may include, for example, axial length, corneal power, corneal power index, and anterior chamber depth. In an aspect, the ocular measurement parameters may include intraoperative aberrometry measurements such as sphere, cylinder, and axis of the eye.

In block 1020, the method 1000 includes determining an intraocular lens power based on a formula using the at least two ocular measurement parameters. For example, the formula component 910 may determine the intraocular lens power based on the formula using the at least two ocular measurement parameters. For instance, in block 1022, determining the intraocular lens power based on the formula may optionally include determining a relevant portion of a super surface including ideal or near ideal portions of a plurality of intraocular lens selection formulas based on a range of the at least two ocular measurement parameters most suitable to each individual intraocular lens selection formula.

In block 1030, the method 1000 may include determining an estimated error of the formula using a deep learning machine trained on verified post-operative results including post-operative refractions corresponding to intraocular lens powers. In an aspect, for example, the neural network 920 may determine the estimated error of the formula. The neural network 920 may have been trained on training sets 930 including verified post-operative results including post-operative refractions corresponding to intraocular lens powers. The verified post-operative results may be obtained from a measurement device such as an autorefractor or a wavefront analyzer.

In block 1040, the method 1000 includes adjusting the lens selection parameter based on the estimated error. In an aspect, for example, the formula component 910 may adjust the lens selection parameter based on the estimated error. For instance, the formula component 910 may subtract the estimated error from a user input lens selection parameter.

In block 1050, the method 1000 includes redetermining the intraocular lens power based on the formula and the adjusted lens selection parameter. In an aspect, for example, the formula component 910 may redetermine the intraocular lens power based on the formula and the adjusted lens selection parameter. For instance, the block 1050 may also include the optional block 1022.

In block 1060, the method 1000 may optionally include rendering the super surface including the relevant portion on a display device. For example, the UI 600 may render the super surface including the relevant portion including the at least two measurement parameters and the intraocular lens power.

While aspects of the present disclosure have been described in connection with examples thereof, it will be understood by those skilled in the art that variations and modifications of the aspects of the present disclosure described above may be made without departing from the scope hereof. Other aspects will be apparent to those skilled in the art from a consideration of the specification or from a practice in accordance with aspects of the disclosure disclosed herein.

The invention claimed is:

1. A method for intraocular lens selection, comprising:
   obtaining at least two ocular measurement parameters and a lens selection parameter for an eye;
   determining an intraocular lens power of an intraocular lens for the eye based on a formula using the at least two ocular measurement parameters and the lens selection parameter;
   determining an estimated error of the formula as applied to the eye using a deep learning machine trained on verified post-operative results including post-operative refractions corresponding to intraocular lens powers; and
   recommending an intraocular lens power of the intraocular lens for the eye based on the formula and the trained deep learning machine.

2. The method of claim 1, wherein the lens selection parameter is a target refraction.

3. The method of claim 1, wherein the lens selection parameter is an A-constant.

4. The method of claim 1, wherein the at least two ocular measurement parameters are selected from the group consisting of: axial length, corneal power, corneal power index, and anterior chamber depth.

5. The method of claim 4, further comprising:
   determining a divergence between each the formula for the axial length and corneal power measurements.

6. The method of claim 1, wherein the formula includes one or more of: a Hoffer Q formula, a Holladay I formula, a Haigis formula, and a SRK/T formula, a Barrett Universal II formula, or adjustments thereto.

7. The method of claim 1, wherein the formula is a machine learned formula.

8. The method of claim 1, wherein the deep learning machine is a neural network configured to receive multiple numeric inputs to predict the estimated error of the formula as a single numeric output.

9. The method of claim 8, wherein the multiple numeric inputs include an axial length, at least one keratometry value, and an anterior chamber depth.

10. The method of claim 1, wherein the deep learning machine is trained with verified results exclusively from a particular lens manufacturer.

11. The method of claim 1, wherein the deep learning machine is trained with verified results exclusively from a particular surgeon or practice group.

12. The method of claim 1, further comprising:
receiving verified post-operative results via an administrative portal; and
training the deep learning machine to predict the estimated error of the formula.

13. The method of claim 1, wherein recommending the intraocular lens power based on the formula and the trained deep learning machine comprises:
adjusting the lens selection parameter based on the estimated error; and
redetermining the intraocular lens power based on the formula and the adjusted lens selection parameter.

14. The method of claim 12, wherein adjusting the lens selection parameter comprises setting the adjusted lens selection parameter to a difference between a user input lens selection parameter and the estimated error.

15. The method of claim 12, wherein adjusting the lens selection parameter based on the estimated error comprises limiting a value of the estimated error not to exceed +/−0.5 diopter.

16. An apparatus for intraocular lens selection, comprising:
a memory storing computer-executable instructions; and
a processor communicatively coupled with the memory, the processor and memory configured to:
obtain at least two ocular measurement parameters and a lens selection parameter for an eye;
determine an intraocular lens power of an intraocular lens for the eye based on a formula using the at least two ocular measurement parameters and the lens selection parameter;
determine an estimated error of the formula as applied to the eye using a deep learning machine trained on verified post-operative results including post-operative refractions corresponding to intraocular lens powers; and
recommend an intraocular lens power of the intraocular lens for the eye based on the formula and the trained deep learning machine.

17. The apparatus of claim 16, further comprising an ocular measurement device configured to measure the at least two ocular measurement parameters.

18. The apparatus of claim 17, wherein the ocular measurement device is selected from a group consisting of an ultrasound device and an optical biometer.

19. The apparatus of claim 16, wherein the lens selection parameter is a target refraction.

20. The apparatus of claim 16, wherein the lens selection parameter is an A-constant.

21. The apparatus of claim 16, wherein the at least two ocular measurement parameters are selected from the group consisting of: axial length, corneal power, corneal power index, and anterior chamber depth.

22. The apparatus of claim 21, wherein the memory and the processor are configured to:
determine a divergence between the formula for the axial length and corneal power measurements.

23. The apparatus of claim 16, wherein the formula includes one or more of: a Hoffer Q formula, a Holladay I formula, a Haigis formula, and a SRK/T formula, a Barrett Universal II formula, or adjustments thereto.

24. The apparatus of claim 16, wherein the lens selection formula is a machine learned formula.

25. The apparatus of claim 16, wherein the deep learning machine is a neural network configured to receive multiple numeric inputs to predict the estimated error of the formula as a single numeric output.

26. The apparatus of claim 25, wherein the multiple numeric inputs include an axial length, at least one keratometry value, and an anterior chamber depth.

27. The apparatus of claim 16, wherein the deep learning machine is trained with verified results exclusively from a particular lens manufacturer.

28. The apparatus of claim 16, wherein the deep learning machine is trained with verified results exclusively from a particular surgeon or practice group.

29. The apparatus of claim 16, wherein the memory and the processor are configured to:
receive verified post-operative results via an administrative portal; and
train the deep learning machine to predict the estimated error of the formula.

30. The apparatus of claim 16, wherein to recommend the intraocular lens power based on the formula and the trained deep learning machine, the memory and the processor are configured to:
adjusting the lens selection parameter based on the estimated error; and
redetermining the intraocular lens power based on the formula and the adjusted lens selection parameter.

31. The apparatus of claim 30, wherein to adjust the lens selection parameter, the memory and processor are configured to set the adjusted lens selection parameter to a difference between a user input lens selection parameter and the estimated error.

32. The apparatus of claim 30, wherein to adjust the lens selection parameter, the memory and processor are configured to limit a value of the estimated error not to exceed +/−0.5 diopter.

33. A non-transitory computer-readable medium storing computer executable instructions, comprising instructions to cause a computer to:
obtain at least two ocular measurement parameters and a lens selection parameter for an eye;
determine an intraocular lens power of an intraocular lens for the eye based on a formula using the at least two ocular measurement parameters and the lens selection parameter;
determine an estimated error of the formula as applied to the eye using a deep learning machine trained on verified post-operative results including post-operative refractions corresponding to intraocular lens powers; and
recommend an intraocular lens power of the intraocular lens for the eye based on the formula and the trained deep learning machine.

* * * * *